United States Patent [19]

Nakajima et al.

[11] Patent Number: 5,767,377
[45] Date of Patent: Jun. 16, 1998

[54] METHOD FOR ENHANCING DISEASE AND PEST RESISTANCE OF PLANTS

[75] Inventors: Hiroki Nakajima, San Diego, Calif.; Kenji Oheda, Kyoto, Japan; Toshiya Muranaka; Fumiharu Ishige, both of Toyonaka, Japan

[73] Assignee: Sumitomo Chemical Company, Limited, Osaka-fu, Japan

[21] Appl. No.: 503,584

[22] Filed: Jul. 18, 1995

[30] Foreign Application Priority Data

Jul. 18, 1994 [JP] Japan .................................. 6-165266
Nov. 10, 1994 [JP] Japan .................................. 6-276573

[51] Int. Cl.$^6$ .......................... A01H 5/00; C12N 15/12; C12N 15/62; C12N 15/82
[52] U.S. Cl. .......................... 800/205; 435/69.1; 435/69.6; 435/69.7; 435/69.8; 435/70.1; 435/172.3; 435/206; 536/23.4; 536/23.5
[58] Field of Search .......................... 435/69.1, 70.1, 435/69.6, 69.7, 69.8, 172.3, 206; 536/23.4, 23.5; 800/205

[56] References Cited

FOREIGN PATENT DOCUMENTS 383591   4/1991   Japan .
WO9305645 4/1993  WIPO .

OTHER PUBLICATIONS

Collinge et al., The Plant Journal, 3(1), 31–40 (1993).
Margis–Pinheiro et al., Plant Molecular Biology, 17: 243–253 (1991).
Düring et al., "Transgenic Potato Plants Resistant to the Phytopathogenic Bacterium *Erwinia carotovora*," *The Plant Journal* 3(4), 587–598 (1993).
Trudel et al., "Expression of Active Hen Egg White Lysozyme in Transgenic Tobacco," *Plant Science*, 87, 55–67 (1992).
Tsuchiya et al. 1992. Appl. Microbiol. Biotechnol. 38(1): 109–114.
Brock, T. 1974. pp.36–38 and 71 *In*: Biology of Microorganisms, 2nd edition, Prentice Hall: New Jersey.

*Primary Examiner*—David T. Fox
*Attorney, Agent, or Firm*—Birch, Stewart, Kolasch & Birch, LLP

[57] ABSTRACT

The gene expression in plants is remarkably increased by utilization of human-derived lysozyme and the growth of various pests is effectively inhibited. Thus, there is disclosed an excellent method for enhancing the disease and pest resistance of plants. With the use of this method, the control of disease and pest with agricultural chemicals can be made unnecessary or reduced, and plant breeding can be performed with more saved labor for a shorter period of time, as compared with the conventional plant breeding mainly by crossing.

7 Claims, 3 Drawing Sheets

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid synthetic DNA ( x i ) SEQUENCE DESCRIPTION: SEQ ID NO: 1:

GATTCATCAT GAAAGTTTTC    20

( 2 ) INFORMATION FOR SEQ ID NO: 2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid synthetic DNA ( i x ) SEQUENCE DESCRIPTION: SEQ ID NO: 2:

CGAAAACTTT CATGATG    17

( 2 ) INFORMATION FOR SEQ ID NO: 3:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: Other nucleic acid synthetic DNA ( i x ) SEQUENCE DESCRIPTION: SEQ ID NO: 3:

CGGATCCG    8

( 2 ) INFORMATION FOR SEQ ID NO: 4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid synthetic DNA ( i x ) SEQUENCE DESCRIPTION: SEQ ID NO: 4:

GAAGAGATTG GGTATGGACG GTTACCGTGG    30

( 2 ) INFORMATION FOR SEQ ID NO: 5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid synthetic DNA ( i x ) SEQUENCE DESCRIPTION: SEQ ID NO: 5:

CAACCTTGAA CGTATTGACG GACGTCACGG    30

( 2 ) INFORMATION FOR SEQ ID NO: 6:

( i ) SEQUENCE CHARACTERISTICS:
        ( A ) LENGTH: 396 base pairs
        ( B ) TYPE: nucleic acid
        ( C ) STRANDEDNESS: double
        ( D ) TOPOLOGY: linear ( i i ) MOLECULE TYPE: Other nucleic acid synthetic DNA of
        nonnatural type ( i i i ) FEATURE:
        ( A ) NAME/KEY: peptide -continued ( B ) LOCATION: 1 to 393
( C ) IDENTIFICATION METHOD: by similarity with a known
sequence or to an established consensus sequence ( i x ) SEQUENCE DESCRIPTION: SEQ ID NO: 6:

```
ATG AAA GTT TTC GAA CGT TGT GAA TTG GCC AGA ACT TTG AAG AGA TTG   48
Met Lys Val Phe Glu Arg Cys Glu Leu Ala Arg Thr Leu Lys Arg Leu
 1               5                  10                  15

GGT ATG GAC GGT TAC CGT GGT ATC TCT TTG GCT AAC TGG ATG TGT TTG   96
Gly Met Asp Gly Tyr Arg Gly Ile Ser Leu Ala Asn Trp Met Cys Leu
            20                  25                  30

GCC AAG TGG GAA TCT GGT TAC AAC ACT AGA GCT ACT AAC TAC AAC GCC  144
Ala Lys Trp Glu Ser Gly Tyr Asn Thr Arg Ala Thr Asn Tyr Asn Ala
        35                  40                  45

GGT GAC CGT TCT ACT GAC TAC GGT ATC TTC CAA ATT AAC TCT AGA TAC  192
Gly Asp Arg Ser Thr Asp Tyr Gly Ile Phe Gln Ile Asn Ser Arg Tyr
    50                  55                  60

TGG TGT AAC GAC GGT AAG ACT CCA GGC GCC GTT AAC GCC TGT CAC TTG  240
Trp Cys Asn Asp Gly Lys Thr Pro Gly Ala Val Asn Ala Cys His Leu
65                  70                  75                  80

TCT TGT TCT GCT TTG TTG CAA GAC AAC ATC GCT GAC GCC GTT GCC TGT  288
Ser Cys Ser Ala Leu Leu Gln Asp Asn Ile Ala Asp Ala Val Ala Cys
                85                  90                  95

GCT AAA CGT GTC GTT CGC GAC CCA CAA GGT ATC CGT GCT TGG GTC GCT  336
Ala Lys Arg Val Val Arg Asp Pro Gln Gly Ile Arg Ala Trp Val Ala
            100                 105                 110

TGG CGT AAC CGC TGT CAA AAC CGT GAC GTG CCT CAA TAC GTT CAA GGT  384
Trp Arg Asn Arg Cys Gln Asn Arg Asp Val Pro Gln Tyr Val Gln Gly
        115                 120                 125

TGT GGT GTC TAA                                                   396
Cys Gly Val
    130
```

METHOD FOR ENHANCING DISEASE AND PEST RESISTANCE OF PLANTS

FIELD OF THE INVENTION

The present invention relates to a method for enhancing the disease and pest resistance of plants.

BACKGROUND OF THE INVENTION

The yield of plants is constantly lost in part by the propagation of various pests. To prevent such a loss, many attempts have been made to suppress the propagation of pests by the use of agricultural chemicals or to produce varieties having an enhanced disease and pest resistance by plant breeding, mainly by crossing. The control of diseases and pests using agricultural chemicals is, however, expensive. The conventional plant breeding, mainly by crossing, has disadvantages that available varieties of plants are limited and that an improvement with saved labor for a short period of time is quite difficult.

In recent years, there has been a remarkable progress in the gene engineering techniques, and an attempt has been made to give disease and pest resistance to plants by a method for introducing a gene coding for the disease and pest resistance into the plants. For example, a method for enhancing pest resistance by utilization of T4 phage-derived lysozyme and chicken-derived lysozyme genes is described in JP-A 3-83591/1991.

The use of T4 phage-derived lysozyme in the above method is unfavorable for attaining more excellent protection against diseases and pests because of its high substrate specificity such that it does not act on portions having no combined peptide in the chitin or peptidoglycan chains. Thus, there has been a demand for more effective utilization of lysozyme.

SUMMARY OF THE INVENTION

Under these circumstances, the present inventors have intensively studied and succeeded in constructing an expression cassette having a gene coding for human-derived lysozyme, introducing the expression cassette into plants and obtaining the expression of said gene. Further, they have confirmed that these improved plants exhibit remarkably enhanced disease and pest resistance, thereby completing the present invention.

Thus, the present invention provides a method for enhancing the disease and pest resistance of a plant, comprising introducing into the plant an expression cassette having, in a functionable manner, (1) a promoter region functionable in plants, (2) a region containing a gene for giving human-derived lysozyme protein after its translation, said region (2) being located downstream from said promoter region, and (3) a terminator region functionable in plants; and obtaining the expression of said gene for human-derived lysozyme in said plant.

In a preferred embodiment, the above region containing a gene for giving human-derived lysozyme protein after its translation has, in a functionable manner, a region containing a secretion signal sequence functionable in plants, which is located upstream from the gene for giving human-derived lysozyme protein after its translation.

The present invention further provides an improved plant which has been given disease and pest resistance by the above method for enhancing the disease and pest resistance in a plant; and an expression cassette having, in a functionable manner, (1) a promoter region functionable in plants, (2) a region containing a gene for giving human-derived lysozyme protein after its translation, said region (2) being located downstream from said promoter region, and (3) a terminator region functionable in plants.

Figure 1:
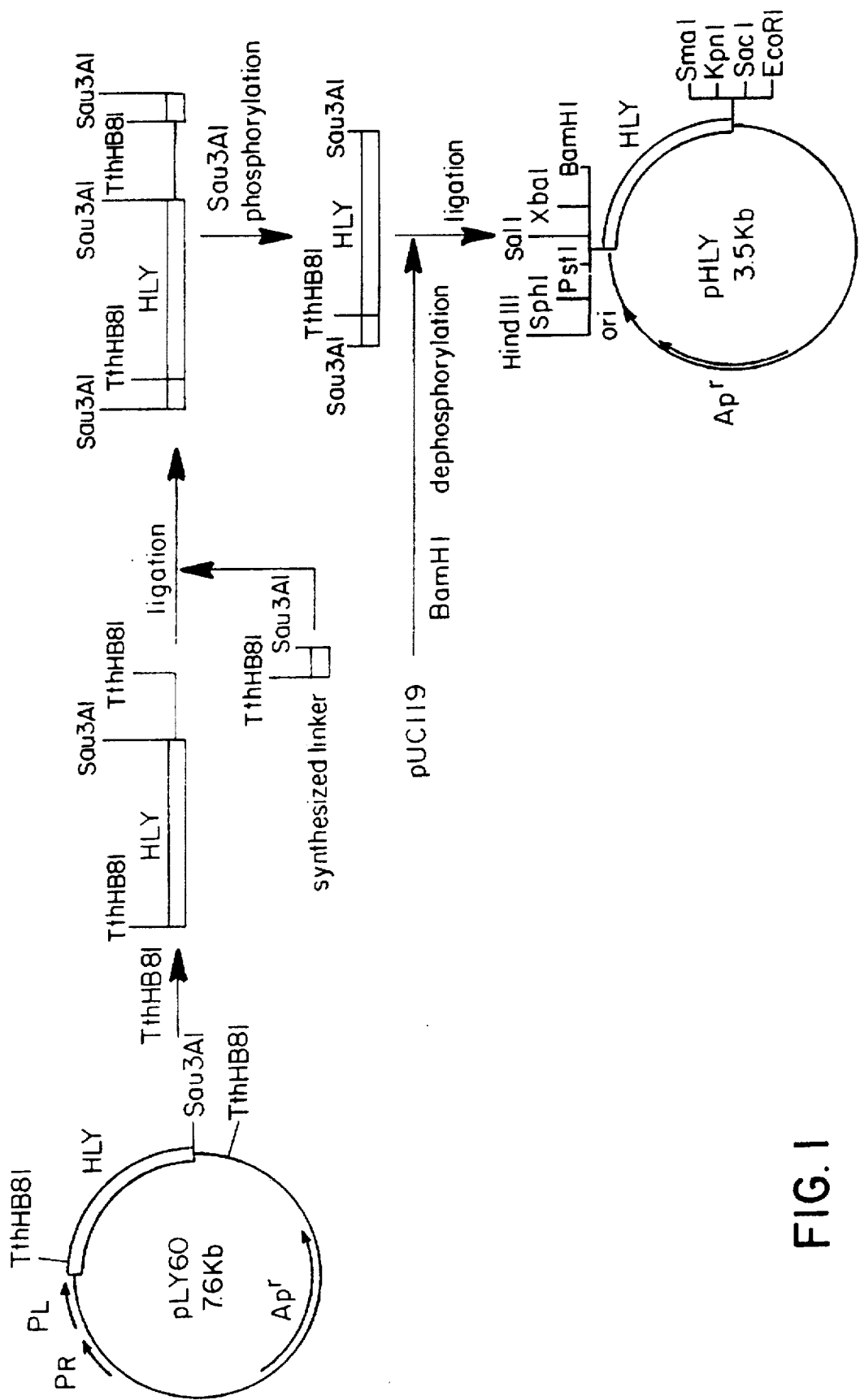
FIG. 1 is a diagram showing the construction from pLY60 to pHLY as a plasmid for introduction of a human lysozyme gene into plants.
Figure 2:
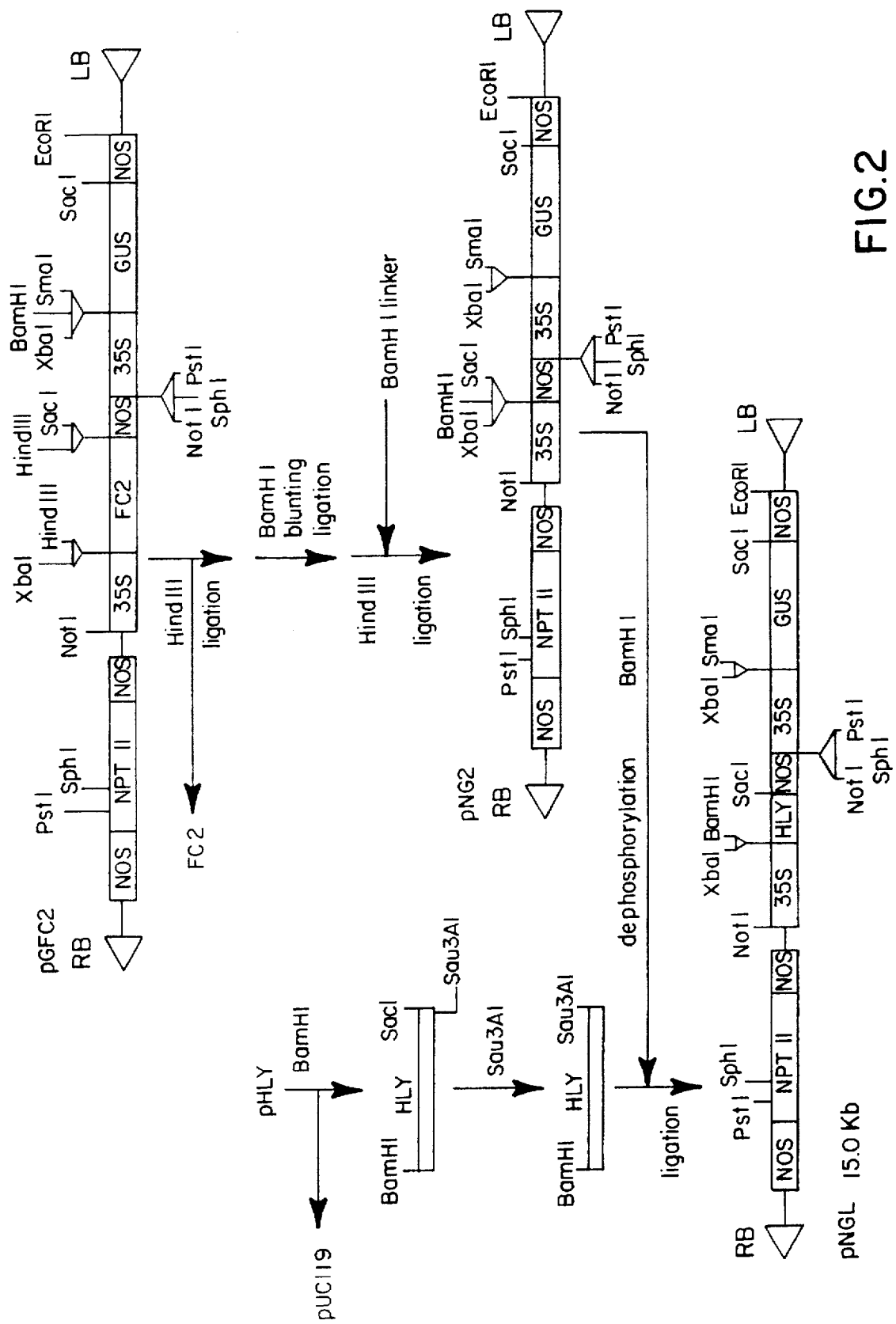
FIG. 2 is a diagram showing the construction from pGFC2 to pNGL as a plasmid for introduction of a human lysozyme gene in plants.

The arrow on the right shows the position of each lane, to which poly(A)+ RNA for human lysozyme was electrophoresed: "lane 1", poly(A)+ RNA extracted from the wild species of tobacco; "lane 2" to "lane 5", poly(A)+ RNA extracted from the screened recombinant tobacco.

DETAILED DESCRIPTION OF THE INVENTION

The gene engineering techniques used in the present invention are conventional ones that can be performed according to the standard methods described in, for example, Sambrook J., Frisch E. F., and Maniatis T. (1989) Molecular Cloning 2nd edition, Cold Spring Harbor Laboratory.

The following is a description on human-derived lysozyme.

As described above, JP-A 3-83591/1991 discloses a method for enhancing pest resistance by utilization of T4 phage-derived lysozyme and chicken-derived lysozyme genes; however, T4 phage-derived lysozyme has high substrate specificity such that it does not act on portions having no combined peptide in the chitin or peptidoglycan chains. The use of T4 lysozyme in the above method is unfavorable for attaining more excellent protection against diseases and pests.

In contrast, human-derived lysozyme used in the present invention has ability to act on various substrates and exhibits the action of effectively inhibiting the propagation of pests. Further, an attempt has been succeeded in an unknown field to express human-derived lysozyme in plants. As an unexpected result, it was found that the expression of a lysozyme protein gene in plants is remarkably enhanced. Referring to the literature (The Plant Journal (1993) vol. 3, no. 4587–598), the degree of expression for T4 phage-derived lysozyme in plants is only 0.001% based on the total amount of poly(A)+ RNA. In contrast, the degree of expression for human-derived lysozyme in plants is at least 0.004% based on the total amount of poly(A)+ RNA, which gives an at least 4-fold increase in the degree of expression. Such an increase in the degree of expression by utilization of a human-derived lysozyme gene is a result that cannot be expected from conventional knowledge. It is, therefore, understood that the use of human-derived lysozyme is an important feature of the present invention. In the following description, human-derived lysozyme is often referred to as human lysozyme.

As used herein, the term "gene for giving human-derived lysozyme protein after its translation" means a gene having the base sequence of a gene naturally residing on the human genome and the base sequence of a gene synthesized from the known amino acid sequence of human lysozyme according to translation codons in other organisms. Particularly preferred are genes suitable for the stability of mRNA and/or produced lysozyme in plants.

The method for preparing these genes can be any conventional one such as a method using polymerase chain reaction (hereinafter referred to as PCR) with the human genome as a template, a total synthesis method using the DNA synthesis technique and a method for codon change by replacing a part of the known human lysozyme gene with a synthetic DNA fragment.

The following is an explanation on the method for obtaining a gene naturally residing on the human genome.

(1) Preparation of Primers

Primers used for amplification of a gene for giving human-derived lysozyme protein after its translation can be obtained mainly by chemical synthesis of DNA. DNA fragments functionable as a primer can also be used, which are obtained by restriction digestion or other techniques. In this case, a pair of primers are used, which correspond to both ends of any base sequence containing the above gene regions. The term "primer" as used herein refers to a DNA fragment containing the 5'-end region of one strand to be synthesized of the desired DNA sequence and necessary for DNA synthesis by DNA polymerase with the complementary strand as a template.

(2) Amplification

The human lysozyme gene fragment is amplified by PCR with a commercially available human genome (Clonetech) as a template. This amplification can be performed under the standard conditions described in general text books. Preferably, the conditions are suitably changed depending upon the base sequences of primers used therein. For example, reference is made to Innis M. A., Gelfand D. H. and Sninsky J. J. (1990) PCR PROTOCOLS, Academic Press Inc.

(3) Cloning of Human Lysozyme Gene

1) Cloning Vector

A number of known cloning vectors can be used. Examples of the cloning vector are plasmid vectors and their derivatives, such as pBR322, pUC18/pUC19, pACYC177 and pACYC184, and phage vectors and their derivatives, such as those derived from M13 phage.

2) Cloning

The cloning is achieved by selecting restriction enzymes to be used according to a combination of restriction sites found in a cloning vector and those found in the DNA fragment obtained by PCR, and causing ligation by ligase.

3) Determination

Whether the desired DNA fragment has been cloned or not can be determined by restriction digestion, PCR or other techniques. The base sequence can be determined with radioactive labels or fluorescent labels by the procedure according to the Maxam-Gilbert method or the Sanger method.

The term "promoter region functionable in plants" as used herein refers to a region functionable in plants, which is associated with the regulation of gene expression, such as initiation of transcription or translation. Examples of such a promoter region are T-DNA derived constitutive promoters such as nopaline synthetase gene (NOS) promoter and octopine synthetase gene (OCS) promoter, and plant virus promoters such as 19S and 35S promoters derived from cauliflower mosaic virus (CaMV). The above promoter region is not particularly limited to these promoters, and any other plant promoters known in the art can also be used.

The term "terminator region functionable in plants" as used herein refers to a region functionable in plants, which is associated with the regulation of gene expression, such as termination of transcription. Examples of such a terminator region are plant terminators such as T-DNA derived NOS terminator, and virus terminators such as those derived from allium virus GV 1 or GV2. The above terminator region is not particularly limited to these terminators, and any other plant or virus terminators can also be used.

The construction of an expression cassette having, in a functionable manner, (1) a promoter region functionable in plants, (2) a region containing a gene for giving human-derived lysozyme protein after its translation, said region (2) being located downstream from said promoter region, and (3) a terminator region functionable in plants can be achieved by an ordinary procedure in which three DNA fragments having regions (1), (2) and (3), respectively, are ligated by the action of ligase with linkers or the like, if necessary. The term "linker" as used herein refers to a synthetic double-stranded DNA fragment making possible the introduction of a recognition site for the desired restriction enzyme after the ligation to the desired DNA terminus.

The expression cassette thus constructed is a gene construction in which the region containing a gene sequence for giving human-derived lysozyme protein after its translation is combined in a functionable manner with the region associated with the regulation of gene expression and which can cause the expression of the desired human-derived lysozyme protein. The selection of a region associated with the regulation of gene expression, which is specifically functionable in particular plants or in particular plant organs makes it possible to obtain improved plants in any form of expression. For example, a functionable combination of a region associated with the regulation of gene expression, such as a promoter specifically functionable in leaves, and a region containing a gene sequence for living human-derived lysozyme protein after its translation, makes it possible to construct a leaf-specific expression cassette of human lysozyme. Further, a functionable combination of a plant virus-derived region having no tissue specificity, which is associated with the regulation of gene expression, and a region containing a gene sequence for giving human-derived lysozyme protein after its translation, makes it possible to construct an expression cassette of human lysozyme for expression in all parts of a plant.

If necessary, a region containing a secretion signal sequence functionable in plants may be combined, in a functionable manner, upstream from the region containing a gene sequence for giving human-derived lysozyme protein after its translation.

The constructed expression cassette can be introduced into various plants, examples of which are monocotyledonous plants such as rice (*Oryza sativa*), corn (*Zea mays*), sorghum (*Sorghum vulgare*), rye (*Secale cereale*), barley (*Hordeum vulgare*), wheat (*Triticum aestivum*) and onion (*Allium cepa*); and dicotyledonous plants including leguminous plants such as soybean (*Glycine max*), pea (*Pisum sativun*), kidney bean (*Phaseolus vulgaris*) and alfalfa (*Medicago sativa*); solanacous plants such as tobacco (*Nicotiana tabacum*), tomato (*Lycopersicon esculentum*) and potato (*Solanum tuberosum*); cruciferous plants such as rapeseed (*Brassica campestris*), cabbage (*Brassica oleracea*) and mustard (*Brasicca juncea*); cucurbitacous plants such as melon (*Cucumis melo*), cucumber (*Cucumis sativus*) and pumpkin (*Cucurbita spp.*); umbelliferous plants such as carrot (*Daucus carota*) and celery (*Apium graveolens*); and compositous plants such as lettuce (*Lactuca scariola*). The introduction of an expression cassette into a plant can be achieved by an ordinary procedure, for example, a technique utilizing the infection of Agrobacterium which is a kind of soil bacteria; a technique for introducing genes into protoplasts by electroporation; or a technique for introducing genes into plant tissues or embryos with a particle gun. The plant having the expression cassette constructed and introduced thereinto is reproduced according to an ordinary procedure used in the plant tissue cultivation technique to obtain a whole plant. Such a procedure is described in, for example, Gelvin S. B., Schilperoort R. A. and Verma D. P. S. (1988) Plant Molecular Biology/Manual, Kluwer Academic Publishers.

The following are two examples of the gene introduction in plants.

1. Gene Introduction into Rice The introduction of a gene into rice is achieved by electroporation. From the suspension cultured cells of rice that has been aseptically subcultured, protoplasts are prepared by treatment of these cells with an cell wall digesting enzyme. These protoplasts are mixed with plasmid DNA for expression of human lysozyme (i.e., expression cassette constructed as described above) and plasmid DNA for drug (e.g., antibiotic) resistance marker, and then given electric stimuli to introduce the plasmid DNA for expression of human lysozyme into the protoplasts. These protoplasts are aseptically cultured for screening on MS medium containing a drug such as an antibiotic, and a plant hormone. The colonies formed on the medium are further screened on antibiotic-containing MS medium to obtain regenerated plants each having a drug (e.g., antibiotic) resistance gene introduced therein. From these screened plants, genome DNA is prepared, and plants each having the human lysozyme gene inserted thereinto are screened by PCR or the Southern blot analysis.

2. Gene Introduction into Carrot

When the introduction of a gene into carrot is performed by the use of Agrobacterium, carrot seeds are aseptically germinated, and their hypocotyl slices are infected with Agrobacterium having a binary vector that contains the human lysozyme gene and the expression cassette for drug (e.g., antibiotic) resistance marker. After the infection these slices were cultured for screening on MS medium containing a plant hormone and an antibiotic to obtain transformed calli. These calli are grown on MS medium to obtain regenerated plants.

When the introduction of a gene into carrot is performed by electroporation, protoplasts are prepared from suspension cultured cells of carrot by treatment of these cells with a cell wall digesting enzyme. These protoplasts are mixed with plasmid DNA for expression of human lysozyme (i.e., expression cassette constructed as described above) and plasmid DNA for drug (e.g., antibiotic) resistance marker, and then given electric stimuli to introduce the plasmid DNA for expression of human lysozyme into the protoplasts. These protoplasts are aseptically cultured for screening on MS medium containing a drug such as an antibiotic, and a plant hormone. The colonies formed on the medium are further screened on antibiotic-containing MS medium to obtain regenerated plants each having a drug (e.g., antibiotic) resistance gene introduced thereinto. From these screened plants, genome DNA is prepared, and plants each having the human lysozyme gene inserted thereinto are screened by PCR or the Southern blot analysis.

According to the method of the present invention, it is possible to enhance the resistance of plants to various pests.

Examples of the pathogenic fungi for plants are Myxomycota or Eumycota such as Mastigomycotina, Zygomycotina, Ascomycotina, Basidiomycotina and Deuteromycotina. Some examples of the disease caused by these fungi are as follows:

Late blight: Phytophthora

Downy mildew: Peronospora, Peronosclerospora, Bremia, Plasmopara, Sclerophthora, Sclerospora Powdery mildew: Sphaerotheca, Erysiphe, Podosphaera, Microspaera, Uncinula Scab: Gibberella Loose smut: Ustillago, Tilletia Rust: Puccinia Blast: Pyricularia Anthracnose: Colletotrichum Gray mold: Botrytis Seedling blight: Pythium Stem rot: Gaeumannomyces Examples of the pathogenic bacteria for plants are Pseudomonadaceae, Rhizobiaceae, Enterobacteriaceae, Streptomycetaceae, Nocardiaceae and Spiroplasmataceae.

The method of the present invention can also be applied to the control of animal pests such as arthropods (e.g., insects), mites, and nematodes, although it can be particularly expected to attain higher resistance to bacteria and fungi.

The method of the present invention is based on the novel finding that the gene expression in plants is remarkably increased by utilization of human-derived lysozyme and the growth of various pests is effectively inhibited. Thus, it is an excellent method for enhancing the disease and pest resistance of a plant. With the use of this method, the disease and pest control with agricultural chemicals can be made unnecessary or reduced, and plant breeding can be performed with more saved labor for a shorter period of time, as compared with the conventional plant breeding, mainly by crossing.

The present invention will be further illustrated by the following Examples, which are not to be construed to limit the scope thereof.

EXAMPLE 1

Preparation of Human Lysozyme Gene

A plasmid for introduction of a human lysozyme gene in plants was prepared by the use of plasmid pLY60 (disclosed in JP-A 2-27988/1990) containing the human lysozyme gene, which had been prepared for large-scale production of human lysozyme by expression in microorganisms. The human lysozyme gene contained in the plasmid pLY60 was a gene (SEQ ID NO: 6) synthesized on the basis of codons for use in yeast.

The plasmid pLY60 was digested with restriction enzyme Tth HB81, which afforded a DNA fragment containing the human lysozyme gene (i.e., lysozyme gene having a partial deletion of the 5' base sequence). To provide restriction sites for supplying the deleted 5' base sequence and introducing the DNA fragment into a cloning vector, the following synthetic DNA linkers were prepared (SEQ ID NOs: 1 and 2).

LY-1 (19 mer) 5'-GATTCATCATGAAAGTTTTC-3'

LY-2 (17 mer) 5'-CGAAAACTTTCATGATG-3'

The lysozyme gene having a partial deletion of the 5' base sequence and the synthetic DNA linker were ligated with T4 DNA ligase. The resultant DNA fragment was digested with restriction enzyme Sau 3AI, and both DNA ends were phosphorylated with T4 DNA kinase. The DNA fragment (403 bp) containing the human lysozyme gene thus obtained was separated and recovered by agarose gel electrophoresis, and then ligated to commercially available cloning vector pUC119 (Takara Shuzo) that had been previously digested with restriction enzyme Bam HI, which afforded plasmid pHLY (see FIG. 1). The base sequence surrounding the synthetic DNA linker inserted above were analyzed by a fluorescent DNA sequencer (Applied Biosystems, model 373A) based on the dideoxy method, and it was determuned that the desired gene fragment was inserted in the plasmid pHLY (SEQ ID NO: 6 shows the total base sequence of the human lysozyme gene inserted in pHLY. The region extending from base nos. 4 to 393 is a coding region for human lysozyme. ATG of base nos. 1 to 3 is the initiation codon for translation).

EXAMPLE 2

Construction of Plasmid to be Introduced into Plant (1) Construction of pNG2

The plasmid pGFC2 (disclosed in JP-A 6-98655/1994) used for expressing in plants a fused enzyme having cytochrome p450 and NADPH-P450 reductase within the same molecule was digested with restriction enzyme Hind III to remove the fused enzyme gene fragment, and then ligated again with T4 DNA ligase to prepare plasmid pNG1. The plasmid pNG1 was digested with Bam HI, treated with T4 DNA polymerase to make the digested ends blunt, and then ligated again with T4 DNA ligase to remove the Bam HI sites. This plasmid was further digested with Hind III and ligated to the commercially available Bam HI linker (SEQ ID NO: 3) with T4 DNA ligase to prepare plasmid pNG2.

Bam HI linker: 5'-CGGATCCG-3'

(2) Construction of Plasmid pNGL to be Introduced into Plant

The plasmid pHLY was digested with Bam HI and Sac I, and a DNA fragment containing the human lysozyme gene was recovered. This fragment was further digested with Sau 3AI, and ligated to Bam HI-digested pNG2 with T4 DNA ligase to prepare plasmid pNGL for introduction of the human lysozyme gene into plants (see FIG. 1). This plasmid had kanamycin resistance gene (NPTII) and β-glucuronidase gene (GUS) as a screening marker gene, and the fragment containing the human lysozyme gene was inserted between the both genes. Therefore, the screening of clones having kanamycin resistance and GUS activity makes it possible to give clones for higher expression of the human lysozyme gene.

EXAMPLE 3

Introduction of Expression Plasmid into Plant

The plasmid pNGL obtained in Example 2 was introduced into *Agrobacterium tumefaciens* (strain LBA4404; having streptomycin resistance and rifampicin resistance: Clonetech) that had been previously made competent by calcium chloride treatment. The transformants were obtained by utilizing the kanamycin resistance given by NPTII contained in the introduced plasmid and screening on L medium (bacto-trypton 10 g, yeast extract 5 g, NaCl 5 g, distilled water 1 liter (pH 7.0)) containing 300 µg/ml of streptomycin, 100 µg/ml of rifampicin and 25 µg/ml of kanamycin.

The transformant *Agrobacterium tumefaciens* was cultured over a whole day and night at 28° C. on L medium containing 300 µg/ml of streptomycin, 100 µg/ml of rifampicin and 25 µg/ml of kanamycin. The bacterial cell suspension obtained was used for infection of small tobacco leaf disks by the ordinary procedure described in Gelvin S. B.,
Schilperoot R. A. and Verma D. P. S. (1988) Plant Molecular Biology/Manual, Kluwer Academic Publishers.

The infected small leaf disks were cultivated on MS-NB agar medium for 4 days. On the 4th day they were transferred to MS-NB agar medium containing cefotaxime (500 µg/ml) for disinfection of Agrobacterium. On the 11th day they were further transferred to MS-NB agar medium containing cefotaxime (500 µg/ml) and kanamycin (100 µg/ml) for starting the screening of transformants. After about 4 weeks, green seedlings after shoot formation were separated by cutting from the small leaf disks, and transplanted to MS agar medium containing cefotaxime (500 µg/ml). The screening with kanamycin was further continued, while repeating the transplanting, and recombinant plants were obtained.

EXAMPLE 4

Measurement of GUS Activity of Recombinant Plant

The GUS activity was measured by the fluorescence method with 4-methylumbelliferylglucuronic acid as a substrate. About 100 mg of leaf fragments of the recombinant plants were put in an Eppendorf tube, and the tissues were thoroughly ground in 100 µg/ml of the extraction buffer (50 mM phosphate buffer, pH 7.0, 10 mM EDTA, 0.1% Triton X-100, 0.1% Sarkosyl, 10 mM mercaptoethanol) with a homogenizer. The mixture was centrifuged at 12,000 rpm (10,000×g) for 5 minutes, and the supernatant was transferred as an extract to another Eppendorf tube. Then, 500 µl of the substrate solution (1 mM 4-methylumbelliferyl-β-D-glucuronide; dissolved in the extraction buffer) and 50 µl of the extract were mixed, and the reaction was allowed to proceed at 37° C. Every given reaction times (e.g., at 0, 10, 20 and 30 minutes) sampling was performed several times in 100 µl portions, and the reaction was suddenly stopped by mixing each sample with 900 µl of the stop solution (0.2M aqueous $Na_2CO_3$ solution). Using a spectrofluorometer (HITACHI, model F-2000), these samples were measured for fluorescence intensity, and screening was performed for recombinant plants exhibiting relatively high GUS activity as determined from the increasing rate of fluorescence intensity.

EXAMPLE 5

Determination of Human Lysozyme Gene Insertion into Screened Recombinant Plant Genome (1) Preparation of Genomic DNA from Screened Recombinant Plant About 0.5 g of leaf fragments of the screened recombinant tobacco were thoroughly ground in an Eppendorf tube with a homogenizer. The mixture was mixed with 0.5 ml of 2× CTAB solution [2% cetyltrimethylammonium bromide (CTAB), 100 mM Tris-HCl (pH 8.0), 20 mA EDTA, 1.4M NaCl, 1% polyvinylpyrrolidone (PVP)], and then kept at 65° C. for 5 minutes. To this mixture was added 0.5 ml of a mixed solution of chloroform and isoamyl alcohol (24:1), followed by mild mixing for 5 minutes. The mixture was centrifuged at 12,000 rpm (10,000×g) for 10 minutes, and the upper layer was transferred to another Eppendorf tube, to which 0.5 ml of isopropyl alcohol was added. DNA deposited by centrifugation at 12,000 rpm (10,000×g) for 15 minutes was separated and dissolved in 200 µl of TE (10 mM Tris-HCl (pH 8.0), 1 mM EDTA). Then, 10 µg/ml of RNaseA was added thereto, and the reaction was allowed to proceed at 37° C. for about 30 minutes to ensure RNA decomposition. After completion of the reaction, the reaction mixture was extracted with a mixed solution of phenol, chloroform and isoamyl alcohol (25:24:1) at the same volume, and the upper layer was recovered in an Eppendorf tube. Then, 1/10 volume of 3M sodium acetate (pH 5.2) and 2.5-fold volume of ethanol were added thereto, and the mixture was centrifuged at 12,000 rpm (10,000×g) for 15 minutes, which afforded 5 µg of genomic DNA.

(2) Determination of Human Lysozyme Gene Insertion by PCR

The amplification of the human lysozyme gene fragment was performed by PCR using 50 ng of genomic DNA of the screened recombinant tobacco obtained by the above procedure as a template and two synthetic PCR primers having the following base sequences (SEQ ID NOs: 4 and 5):

N1 (30 mer) 5'-GAAGAGATTGGGTATGGACG GTTACCGTGG-3'

C1 (30 mer) 5'-CAACCTTGAACGTATTGACG GACGTCACGG-3' and a part of the PCR reaction mixture was analyzed by agarose gel electrophoresis. The amplification of the human lysozyme gene was observed in the screened recombinant tobacco.

EXAMPLE 6

Determination of Human Lysozyme Gene Expression in Screened Recombinant Plant (1) Preparation of Poly(A)+ RNA from Screened Recombinant Plant One gram of tobacco leaf tissue was ground in liquid nitrogen with mortar and pestle, and then suspended in 10 ml of ISOGEN (Nippon Gene). To this suspension was added 2 ml of chloroform, and the mixture was thoroughly stirred and then centrifuged at 10,000 rpm (7,500×g) for 10 minutes to separate the aqueous layer. The aqueous layer was mixed with 5 ml of isopropanol, and the deposited RNA was separated by centrifugation at 10,000 rpm (7,500×g) for 10 minutes. The RNA was washed with 5 ml of 75% ethanol, and then dissolved in 500 µl of the eluent (10 mM Tris-HCl (pH 7.5), 1 mM EDTA, 0.1% SDS), to which 500 µl of oligotex-dt 30 (Takara Shuzo) was added. The mixture was heated at 65° C. for 5 minutes, and then rapidly cooled on ice for 3 minutes, to which 100 µl of 5M NaCl was added. After kept at 37° C. for 10 minutes, the mixture was centrifuged at 12,000 rpm (10,000×g) for 5 minutes to remove the supernatant. The precipitate was suspended again in 500 µl of TE, subjected to heat treatment at 65° C. for 5 minutes, and then rapidly cooled on ice for 3 minutes. The supernatant was recovered by centrifugation at 12,000 rpm (10,000×g) for 5 minutes, and extracted with 500 µl of a mixed solution of phenol, chloroform and isoamyl alcohol. Then, poly(A)+ RNA was purified twice by ethanol precipitation.

(2) Detection of Transcription Product of Human Lysozyme Gene by Northern Blotting and Northern Hybridization According to the procedure described in Sambrook J., Frisch E. F., Maniatis T. (1989) Molecular Cloning 2nd edition, Cold Spring Harbor Laboratory, Northern brotting and Northern hybridization were performed to detect the desired gene expression. The poly(A)+ RNA was subjected to electrophoresis (100 mV, 1 hour) on 1.2% (w/v) agarose gel containing formaldehyde, and the RNA separated after the electrophoresis was transferred from the gel to a nylon membrane.

Figure 3:
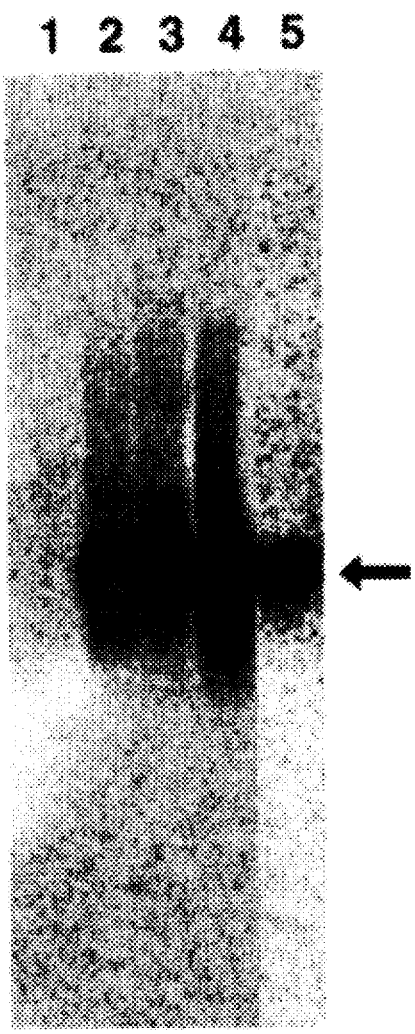
FIG. 3 is a view showing the results of a detection test for expression of a human lysozyme gene by the Northern blot method.

The human lysozyme gene fragment obtained by digestion of pNGL with Bam HI and Sac I was used as a template, and a labelled probe was prepared using random primers and the Klenow fragment. The poly(A)+ RNA of human lysozyme was detected by hybridization of the RNA fixed on the nylon membrane with the labelled probe, and it was determined that the human lysozyme gene introduced into the screened recombinant tobacco had been expressed. Four clones of the recombinant tobacco exhibiting a relatively high degree of expression were selected (see FIG. 3).

According to the above procedure, the signal intensity from the screened recombinant tobacco was compared with the signal intensity corresponding to the human lysozyme gene fragment that had been subjected at the same time to electrophoresis and Northern blot analysis, and the weight of mRNA for human lysozyme expressed in the screened recombinant tobacco was calculated to be at least 75 pg. The poly(A)+ RNA at an amount equivalent to 2 µg was electrophoresed on each lane, and the degree of expression for human lysozyme in the recombinant tobacco was found to be at least 0.004% based on the total amount of poly(A)+ RNA. In contrast, the degree of expression for T4 phage-derived lysozyme in plants was only 0.001% based on the total amount of poly(A)+ RNA (see The Plant Journal (1993) vol. 3, no. 4587–598).

EXAMPLE 7

Determination of Human Lysozyme Protein Accumulation in Screened Recombinant Plant First, 0.2 g of the recombinant tobacco tissue screened in Example 6 was ground in a solution containing 2.5% SDS, 10% sucrose and 50 mM $CaCl_2$ with mortar and pestle, and then centrifuged at 12,000 rpm (10,000×g) for 10 minutes to separate the supernatant as an extract. This extract was subjected to electrophoresis (40 mV, 1 hour) on 15–25% (w/v) density gradient polyacrylamide gel containing SDS, and the separated protein was electrically transcribed on a nitrocellulose membrane. The protein thus transcribed on the membrane was detected by reaction with the commercially available anti-serum to human lysozyme (Nordic). It was determined that the human lysozyme protein was accumulated in the screened recombinant tobacco.

EXAMPLE 8

Test of Screened Recombinant Plant for Resistance to Powdery Mildew

A conidium suspension ($1\times10^4$ spores/ml) prepared from the leaves that had been previously infected with *Erysiphe cichoracearum* was inoculated on the tested plants with a sprayer for chromatography. After about one week, the infected area of leaves was measured. The tested plants were evaluated for the infected area ratio showing the ratio of infected area to leaf area. The results are shown in Table 1. With respect to the wild species of tobacco and the recombinant tobacco screened in Example 6, the infected area ratio on the average of three independent test results was compared. The results are shown in Table 1. The average infected area ratio of the screened recombinant tobacco was remarkably reduced relatively to that of the wild species of tobacco (92% reduction on the average). In particular, two clones (recombinant tobacco plants 3 and 4 in Table 3) had an approximately 100% control effect.

TABLE 1

Resistance to powdery mildew of tobacco plants having human lysozyme gene introduced thereinto

| Plant | | Average infected area ratio (%) | Percent reduction (%) |
|---|---|---|---|
| Wild species of tobacco | | 8.02 | — |
| Recombinant tobacco | 1 | 1.53 | 81 |
| | 2 | 0.67 | 92 |
| | 3 | 0.06 | 99 |
| | 4 | 0.28 | 97 |

The average percent reduction of the infected area in the screened recombinant tobacco was 92%

EXAMPLE 9

Test of Screened Recombinant Plant for Resistance to Wild Fire

As the tested plants were used the wild species of tobacco and the recombinant tobacco screened in Example 6. A 10-fold dilution of the overnight culture suspension ($1\times10^8$ cells/ml) of *Pseudomonas syringae* pv. *tabaci* was inoculated on 10 spots of the tested plant leaves in 10 μl portions per spot. The tested plants thus inoculated with the fungi were grown in an air conditioning room (25° C., light place, 16 hours/23° C., dark place, 8 hours), while keeping them under high humidity conditions by covering them with vinyl bags of an appropriate size. After one week, the infected area in the leaf parts of the plants (the area of yellowing lesions around the inocculation spots) were measured. The infected area was determined by measurement of the length and breadth of appearing, yellowing lesions with slide calipers and calculation of the elliptic area [3.14×(length)×(breadth) /4]. The results are shown In Table 2. The average infected area of the screened recombinant tobacco was remarkably reduced relatively to the average infected area of the wild species of tobacco (80% reduction on the average).

TABLE 2

Resistance to wild fire of tobacco plants having human lysozyme gene introduced thereinto

| Plant | | Average infected area ($mm^2$) | Standard deviation ($mm^2$) | Percent reduction (%) |
|---|---|---|---|---|
| Wild species of tobacco | | 182 | 37 | — |
| Recombinant tobacco | 1 | 53 | 34 | 71 |
| | 2 | 31 | 21 | 83 |
| | 3 | 27 | 11 | 85 |

The average percent reduction of infected area in the screened recombinant tobacco was 80%.

The following are compositions of MS medium and MS-NB medium used in the above Examples.

1. MS Medium

MS medium was prepared by mixing 10 ml of [MS-1 100-fold concentrate], 10 ml of [MS-2 100-fold concentrate], 10 ml of [MS-3 100-fold concentrate], 10 ml of [MS-4 100-fold concentrate], 20 ml of [MS-5 50-fold concentrate], 20 ml of [MS-6 50-fold concentrate] and 10 ml of [MS-7 100-fold concentrate], adjusting the pH to 5.8, and then making the final volume into 1000 ml.

[MS-1 100-fold concentrate]

$Na_2EDTA$, 1865 mg; $FeSO_4 \cdot H_2O$, 1390 mg; distilled water, 500 ml

[MS-2 100-fold concentrate]

$MgSO_4 \cdot 7H_2O$, 18,500 mg; $MnSO_4 \cdot H_2O$ 1115 mg; $ZnSO_4 \cdot 7H_2O$, 430 mg; $CuSO_4 \cdot 5H_2O$, 1250 μl (1 mg/ml stock); distilled water, 500 ml

[MS-3 100-fold concentrate]

$CaCl_2 \cdot 2H_2O$, 22,000 mg; KI, 42 mg; $CoCl_2 \cdot H_2O$, 1250 μl (1 mg/ml stock); distilled water, 500 ml

[MS-4 100-fold concentrate]

$KH_2PO_4$, 8500 mg; $H_3BO_3$, 310 mg; $Na_2MoO_4 \cdot H_2O$, 1250 μl (1 mg/ml stock); distilled water, 500 ml

[MS-5 50-fold concentrate]

$NH_4NO_3$, 82,500 mg; distilled water, 1000 ml

[MS-6 50-fold concentrate]

$KNO_3$, 95,000 mg; distilled water, 1000 ml

[MS-7 100-fold concentrate]

Myo-inositol, 5000 mg; thiamin hydrochloride, 5 mg; pyridoxin hydrochloride, 25 mg; nicotinic acid, 25 mg; glycine, 100 mg; distilled water, 1000 ml 2. MS-NB Medium MS-NB medium was prepared by adding 0.1 mg/ml NAA (1-naphthalene acetic acid) and 1.0 mg/ml BA (6-benzylaminopurine) to the above MS medium.

What is claimed is:

1. A method for enhancing the disease and pest resistance of a plant, comprising introducing into the plant an expression cassette comprising as operably linked components: (1) a promoter region functional in plants, (2) a region containing a gene encoding human-derived lysozyme protein, said region (2) being located downstream from said promoter region, and (3) a terminator region functional in plants; and obtaining the expression of said gene for human-derived lysozyme in said plant.

2. The method according to claim 1, wherein the region containing a gene encoding human-derived lysozyme protein comprises a region containing a secretion signal sequence functional in plants, which is located upstream from the gene for encoding human-derived lysozyme protein.

3. A plant having disease and pest resistance produced by the method according to claim 1.

4. An expression cassette comprising as operably linked components: (1) a promoter region functional in plants, (2) a region containing a gene encoding human-derived lysozyme protein, said region (2) being located downstream from said promoter region, and (3) a terminator region functional in plants.

5. A method according to claim 1 or 2, wherein the plant is monocotyledonous or dicotyledonous.

6. A method according to claim 1 or 2, wherein the disease resistance to phytopathogenic fungi and bacteria is enhanced.

7. A method for enhancing the disease resistance to phytopathogenic fungi and bacteria of a plant, comprising introducing into the plant an expression cassette comprising as operably linked components: (1) a promoter region functional in plants, (2) a region containing a gene encoding human-derived lysozyme protein, said region (2) being located downstream from said promoter region, and (3) a terminator region functional in plants; and obtaining the expression of said gene for human-derived lysozyme in said plant.

* * * * *